TODO

(56) References Cited

OTHER PUBLICATIONS

Hou, et al., "Changes in hippocampal synapses and learning-memory abilities in a streptozotocin-treated rat model and intervention by using fasudil hydrochloride," Neuroscience, (2012), vol. 200:120-129.
Human Rights Watch. 2018. They Want Docile: How Nursing Homes in the United StatesOvermedicate People with Dementia. ISBN: 978-1-623-135720. Downloaded May 17, 2019from http://www.hrw.org.
Jacobs, et al., "The structure of dimeric ROCK I reveals the mechanism for ligand selectivity," J Biol Chem., (2006), vol. 281(1): 260-68.
Kamei, et al., "Evaluation of Fasudil Hydrochloride Treatment for Wandering Symptoms in Cerebrovascular Dementia with 31P-Magnetic Resonance Spectroscopy and Xe-Computed Tomography," Clin Neuropharmacol., (1996), vol. 19, No. 5: 428-38.
Kamei, et al., "Effect of fasudil hydrochloride on wandering symptoms of cerebrovascular dementia patients," Neurotherapy, (1996), vol. 13: 43-50.
Kim, et al., Diagnostic Accuracy of Mini-Mental Status Examination and Revised Hasegawa Dementia Scale for Alzheimer's Disease, Dement Geriatr Cogn Disord., (2005), vol. 19: 324-30.
Klein, et al., "Wandering behaviour in community-residing persons with dementia," Intl J Geriatric Psychiatry, (1999), vol. 14: 272-279.
Knuffman, et al., "Differentiating Between Lewy Body Dementia and Alzheimer's Disease: A Retrospective Brain Bank Study," J Am Med Dir Assoc., (2001), vol. 2: 146-8.
Lai, et al., "Wandering behaviour in people with dementia," J Adv Nurs., (2003), vol. 44(2): 173-182.
Nair, et al., "A simple practice guide for dose conversion between animals and human," J Basic Clin Pharm., (2016), vol. 7: 27-31.
Roman, et al., "Vascular dementia: Diagnostic criteria for research studies, Report of the NINDS-AIREN International Workshop," Neurology, (1993), vol. 43: 250-60.
Roman, Gustavo C., "Facts, myths, and controversies in vascular dementia," J Neurol Sci., (2004), vol. 226: 49-52.
Salardini, Arash, "An Overview of Primary Dementias as Clinicopathological Entities," Semin Neurol., (2019), vol. 39: 153-166.
Sasaguri, et al., "APP mouse models for Alzheimer's disease preclinical studies," EMBO J., (2017), vol. 36, No. 17: 2473-2487.
Sellers, et al., "Amyloid β synaptotoxicity is Wnt-PCP dependent and blocked by fasudil," Alzeimer's & Dementia, (2018), vol. 14: 306-317.
Shibuya, et al., "Effect of Fasudil HCI, a Protein Kinase Inhibitor, on Cerebral Vasospasm," Acta Neurochir Suppl., (2001), vol. 77: 201-4.
Turk, Mari, "The Effect of Rho Kinase Inhibitors on Alzheimer's Disease," Dissertation, Arizona State University, May 2017.
Uehata, et al., "Calcium sensitization of smooth muscle mediated by a Rho-associated protein kinase in hypertension," Nature, (1997), vol. 389: 990-4.
Yamaguchi, et al., "Structural Basis for Induced-Fit Binding of Rho-Kinase to the Inhibitor Y-27632," J Biochem., (2006), vol. 140: 305-11.
Yayama, et al., "Discrepancy between subjective and objective assessments of wandering behaviours in dementia as measured by the Algase Wandering Scale and the Integrated Circuit tag monitoring system," Psychogeriatrics, (2013), vol. 13: 80-87.
Yu, et al., "Fasudil improves cognition of APP/PS1 transgenic mice via inhibiting the activation of microglia and shifting microglia phenotypes from M1 to M2," Chin J Cell Mol Immunol., (2017), vol. 33(12): 1585-1593.
Ceyzeriat, et al., "Learning from the Past: A Review of Clinical Trials Targeting Amyloid, Tau and Neuroinflammation in Alzheimer's Disease," Current Alzheimer Research, (2020), vol. 17: 1-13.
Elliott, et al., "A role for APP in Wnt signalling links synapse loss with β-amyloid production," Translational Psychiatry, (2018), vol. 8: 179.
Logsdon, et al., "Wandering: A Significant Problem Among Community-Residing Individuals with Alzheimer's Disease," The Journals of Gerontology Series B Psychological Sciences and Social Sciences, (1998), vol. 53B, No. 5: P294-9.
Nakagawa, et al., "ROCK-I and ROCK-II, two isoforms of Rho-associated coiled-coil forming protein serine/threonine kinase in mice," FEBS Lett., (1996), vol. 392: 189-93.
Koch, et al., "ROCK inhibition in models of neurodegeneration and its potential for clinical translation," Pharmacology & Therapeutics, (2018), https://doi.org/10.1016/j.pharmthera.2018.03.008.
Nakaoka, et al., "Pacing and Lapping Movements Among Institutionalized Patients With Dementia," Am J Alzheimers Dis Other Demen, (2010), vol. 25: 167-72.
International Search Report of International and Written opinion Patent Application No. PCT/US21/12575 dated Apr. 16, 2021.
Sladojevic, Nikola et al., "ROCK as a therapeutic target for ischemic stroke", Expert Rev Neurother., Dec. 2017, pp. 1167-1177, vol. 17, No. 12.
Yan et al., "Curative effect of Fasudil injection combined with Nimodipine on Alzheimer disease of elderly patients", Journal of Clinical Medicine in Practice, 2011, pp. 92-94, 98, vol. No. 15, Issue No. 13.

METHODS OF TREATING CORTICAL DEMENTIA ASSOCIATED WANDERING

CROSS-REFERENCE TO RELATED APPLICATIONS

This application is claims priority to U.S. Provisional Patent Application No. 62/958,985, filed 9 Jan. 2020, U.S. Provisional Patent Application No. 62/971,697, filed 7 Feb. 2020, and U.S. Provisional Patent Application No. 63/004,305, filed 2 Apr. 2020. Each of these applications is incorporated by reference in its entirety.

BACKGROUND OF THE INVENTION

Wandering is "locomotion behavior having a frequent, repetitive, temporally-disordered, and/or spatially-disordered nature that is manifested in lapping, random, and/or pacing patterns some of which are associated with eloping, eloping attempts, or getting lost unless accompanied." Wandering behavior is associated with many conditions degenerative neurological conditions, such as Huntington's disease (HD), autism spectrum disorder, Down syndrome, progressive supranuclear palsy, corticobasal degeneration, and dementia.

The most common underlying cause of wandering is dementia. The dementia can result, for example, from Parkinson's Disease (PD), Huntington's Disease (HD), amyotrophic lateral sclerosis (ALS), Alzheimer's Disease (AD), Dementia with Lewy Bodies (DLB) and Frontotemporal Dementia (FTD), normal pressure hydrocephalus (NPH) and head injuries, among others. While wandering occurs in all forms of dementia, irrespective of etiology, it occurs at different frequencies and exhibits different quantitative and qualitative features depending on the type of dementia (Cipriani 2014).

There is no standardized assessment tool for diagnosing or assessing wandering. Wandering is frequently captured using the Neuropsychiatric Inventory (NPI) and the Cohen-Mansfield Agitation Inventory, two broad tools for assessing behavioral and psychological symptoms of dementia (Yayama 2013). As an example, the NPI has a single item on wandering: 'pace or wheel around the facility with no reason.' Thus, illustrating its limited utility, the NPI will only detect the repetitive wandering that is characteristic of FTD, but uncommon in AD and rare in VaD (Bathgate 2001; Nakaoko 2010). The Algase Wandering Scale (Algase 2001a), on the other hand, is the only tool for the exclusive assessment of wandering and it is not limited to a specific type/dimension of wandering (Yayama 2013).

Wandering can be described in terms of a variety of dimensions including frequency (persistence), pattern (lapping, random, or pacing), boundary transgressions (elopement), and deficits in navigation or wayfinding (spatial disorientation) (Algase 2001a). Thus, wandering is a general term used to describe many different actions and it is well documented that wandering quantitatively and qualitatively varies with different forms and degrees of dementia (Cipriani 2014).

Wandering is often the reason a dementia patient loses his/her independence and is placed in a long-term-care facility, which not only affects self-esteem and leads to social isolation, but also represents a significant societal cost (Logsdon 1998). Wandering is characterized by excessive, aimless ambulation that frequently leads to nuisance and, more importantly, safety concerns (Lai 2003; Aud 2004). Especially when the patient is able to escape his/her controlled environment, wandering increases the risk of quality of life-affecting injury through falls and other incidents, or even death (Algase 2001a; Wick 2006). Wandering patients have been reported to be "chemically" restrained using antipsychotics or sedation to prevent escape and to control problematic symptoms like wandering (Human Rights Watch 2018). Clearly a goal of any wandering treatment would be avoiding chemical restraint. There are currently no treatments available for wandering of any etiology and so there is a significant need for treatment approaches for wandering.

Among the dementias, VaD is differentiated from other forms of dementia by the presence of one or more vascular causes in the general absence of other pathologies. Specifically, VaD is not a neurodegenerative disease, unlike all other types of dementia (Salardini 2019). Uniquely, the pathophysiology of VaD is not linked to an underlying proteinopathy.

Kamei (1996a) reported on using fasudil in two patients with wandering due to VaD. The patients were treated by the investigator for wandering following participating in a chronic stroke study where they were treated with fasudil. One patient was diagnosed with Binswanger-type cerebral infarction, confirmed by MM imaging. Prior to treatment, the patient had a history of more than 3.5 years of wandering symptoms, consisting primarily of wayfinding problems. The patient could not find his way home. Then, for about a year-and-a-half prior to beginning treatment, the patient was regularly eloping approximately 2-3 times per week. Within weeks of beginning treatment, wandering symptoms disappeared and remained absent for the duration of treatment. When the patient was removed from treatment, wandering symptoms reappeared within weeks. Upon re-treatment, wandering again resolved. The other patient was diagnosed with sequelae of cerebral bleeding and multiple lacunar infarctions, confirmed by MRI, and a diagnosis of "lacunar dementia" (a synonym of Binswanger's; Román 1985) Approximately 5 months after the hemorrhage, the patient began exhibiting wayfinding symptoms, beginning with several episodes of losing his way with frequency increasing to 2-3 times per week over several months. Wayfinding symptoms disappeared quickly and remained absent for the duration of treatment, returning each time treatment was stopped.

The two main subtypes vascular dementia are i) large cortical infarction or multi-infarct dementia (MID) and ii) small vessel disease-related dementia or subcortical vascular dementia. The two patients treated by the Kamei authors both had subcortical vascular dementia, which is caused by disruption of the vasculature in the subcortical white matter-rich areas of the brain. The International Classification of Diseases (10th revision) (ICD-10) criteria for vascular explicitly identifies subcortical vascular dementia as a subgroup [Wetterling et al., *Dementia*. 1994; 5(3-4): 185-188]. Subcortical vascular dementia therefore, incorporates the old entities "lacunar state" and "Binswanger disease" and relates to small vessel disease and hypoperfusion resulting in focal and diffuse ischemic white matter lesion and incomplete ischemic injury. (Erkinjuntti, 1997). On the other hand, most dementia patients suffer from the first type, affecting the cortical regions of the brain, and present with different defects that result from very different pathophysiological processes.

Moreover, both Kamei 1996a patients were sporadic wanderers, wandering 2-3 days per week and they displayed primarily a wayfinding defect, and no other problematic behavior. Kamei also published another paper in 1996

(Kamei 1996b) with substantially the same findings. Prior to these publications, Kamei filed a patent application in Japan (Patent Application 6-293643) based on the same two patients in the publication and a third patient. It should also be noted that Kamei 1996a presented two cognitive measures, the Mini Mental State Exam (MMSE) and the Hasegawa Dementia Score (HDS), which are very similar and usually yield very similar results. In fact, the HDS usually scores dementia patients as more severe than the MMSE (Kim 2005), yet not only were the MMSE scores in Kamei 1996a consistently worse than the HDS, the different scores lead to a dramatically different understanding of the patient population. The HDS suggests that the patients had only mild dementia, whereas the MMSE suggest that they are moderately to severely demented.

There is no evidence that the work of Kamei in subcortical vascular dementia can be extrapolated to cortical forms of dementia or to non-vascular forms of subcortical dementia, nor that it can be extrapolated to persistent wanderers or wanderers without a wayfinding defect. The etiologies, pathologies and symptoms of sub-cortical and cortical vascular dementias are well characterized. Large vessel cortical strokes and subcortical small vessel disease tend to produce different kinds of deficits. Characteristic symptoms of subcortical dementia typically include forgetfulness, slowing of thought processes, mild intellectual impairment, apathy, inertia, depression (sometimes with irritability), loss of recall ability, and the inability to manipulate knowledge. Additionally, subcortical dementia patients have mood disorders. Other behavioral abnormalities like repetitive and compulsive behavior occur in some patients suffering from subcortical dementia. Generally, sub-cortical dementia presentation is more subtle and temporally progressive, often described as defects in executive function in sub-cortical dementia. This includes deficits in speed and "strategic" processing (i.e., attention, planning, and monitoring) in tasks such as memory tasks.

In contrast, cortical vascular dementia is associated with aphasia, apraxia and amnesia.

Memory is impaired in both sub-cortical and cortical vascular dementia. But in cortical vascular dementias, the recall abnormality is due to a failure to encode information properly or decay of memory consolidation. Behavioral changes may include apathy, lack of spontaneity, and perseveration. In contrast, in subcortical disorders exhibit deficits in spontaneous recall, but encoding and storage are largely preserved, and recollection can be aided. Subcortical dementia is characterized by a relatively mild retrograde amnesia that equally affects all time periods because here there is faulty retrieval of successfully stored information. It is the recall deficit that results in wayfinding problems in sub-cortical vascular dementia.

Sub-cortical and cortical dementia are differentially diagnosed. White matter hyperintensities (i.e., sub-cortical) are considered to result from cerebral small vessel disease, especially at larger volumes. This damage can be quantified using the Fazekas scale: 0 (no lesions); 1 (punctiform lesions); 2 (early confluent lesions); and 3 (confluent lesions). A Fazekas score of 1 can be considered normal, whereas scores 2 and 3 indicate the presence of small vessel disease. A score of 3 is abnormal at any age. The presence of confluent lesions in the frontal and parietal lobes is indicative of a large white matter pathology (>25%) and can be used in making a diagnosis of (subcortical) vascular dementia. Lacunar infarcts involving multiple basal ganglia and the frontal white matter, as well as bilateral thalamic lesions are also diagnostic of subcortical vascular dementia.

Strategic large vessel infarctions can indicate cortical dementia when they involve the following territories: bilateral anterior cerebral artery, paramedian thalamic, inferior medial temporal lobe, parieto-temporal and temporo-occipital association areas and angular gyms, superior frontal and parietal watershed areas in the dominant hemisphere.

A central issue with interventions that target cortical dementia is that of association versus causation. In order for an intervention to work in treating a disease, it must interrupt the chain of causation. AD, the most common form of dementia, provides a very instructive case. The two characteristic pathological findings of AD are the extracellular amyloid plaques and inter-neuronal neurofibrillary tangles (NFT).

While Aβ, tau and neuroinflammation are certainly associated with AD, is it not clear they are involved in causation and thus, it is unclear that affecting any of these will have any therapeutic benefit in treating the disease. Based on understanding the familial disease, it is believed that Aβ starts the process of neurodegeneration by inducing Tau pathology, neuroinflammation and finally the neuronal loss that leads to cognitive decline. In other words, Aβ is at the beginning of the causality chain. Stopping Aβ pathology should stop the disease and, so far, most therapeutic approaches have targeted Aβ.

Despite the overwhelming literature showing the promise of targeting Aβ in animal models, however, there have been no products that have been shown to work in AD (Ceyzériat et al., *Current Alzheimer Research* 17: 1-13 (2020). These failures include, notably among many, Anti-Aβ42+Freud's adjuvant, Bapineuzumab, Solanezumab, Aducanumab, Verubecestat, Lanabecestat, Atabecestat, CNP520, Elenbecestat, γ-Secretase inhibitors, Bryostatin and PBT2.

Tau is a less likely target because of the evidence that it is downstream of Aβ, and thus is not causative, and so trials have been less frequent. Notably, of 15 trial targeting tau that have been initiated, already four of them have been stopped.

The role of neuroinflammation, the third putative interventional target, in AD is unclear, likely being beneficial in early-stage disease, but possibly evolving adversely by participating in a loop of pro-inflammatory cytokine production and oxidative stress. While epidemiological studies have suggested that treatment with nonsteroidal anti-inflammatory drugs (NSAIDs) reduce the risk of developing AD and they can decrease amyloid load in transgenic models, to date prospective studies testing anti-inflammatory drugs have shown no beneficial effect on cognition in AD. Studies targeting neuroinflammation are ongoing, but early results are not promising. Neflamapimod, a selective inhibitor of p38 mitogen-activated protein kinase showed efficacy in an animal model, but it had no effect on Aβ deposition in humans and failed its primary endpoint of improving episodic memory in Phase 2, despite reducing tau in the cerebrospinal fluid.

In view of the number of clinical failures of compounds that seemed promising in animal models, a grave degree of skepticism should be applied in interpreting animal data. Even aside from the obvious issues of differences in brain complexity between rodents and humans, many of the existing models bear only a passing resemblance to the human condition. Many things can cause neural degeneration in animals and many putative drugs can halt that neural degeneration, but the underlying pathophysiology and chain of causation is unknown and it is there that a disease modifying intervention must act. It is crucial, therefore, that animal models, with their known deficiencies in the best of cases, as closely resemble the human disease as possible, in both pathology and clinical presentation.

There are a number of publications looking at the use of rho kinase inhibitors in various models of AD/dementia. Most models are deficient in basic properties. Some models involve the direct induction of neurotoxicity with agents like streptozotocin or even by direct injection of amyloid-beta into the brain. While these models may exhibit certain AD-like properties, they are just models of neural degeneration and cannot predict treatment of AD itself. Even the transgenic models are deficient. For example, there are a number of transgenic mice that only develop amyloid plaques without NFTs, such as the APP/PS-1 mouse, perhaps the most widely reported transgenic model. There are also mice that develop tauopathies, without amyloid plaques, such as the rTG4510 tau mouse. AD is characterized by the presence of both. Some publications use unrealistic routes of administration (e.g., intraventricular injection) and many do not use appropriate dosing. In this regard, standard formulas exist for converting doses used in animals to the same dose in humans. Human equivalent dose can be calculated, for example, using Table 1 of Nair & Jacob, *J Basic Clin Pharm.* 7:27-31 (2016), which are the same conversions used by the US FDA. Becker, *Alzheimers Dis.* 15:303-325 (2008) discusses the criticality of dose in successful AD drug development and points to it as a failure point in AD drug development.

Published literature exists in which fasudil is administered in animal models of dementia. But these studies are deficient for many of the same reasons. Namely, the animal models do not faithfully recapitulate human disease, partly due to species differences in neuroanatomy (Sasaguri 2017) and partly due to the deficient basic pathological bases of the models, described above. In addition, some fail to use physiologically relevant doses and, importantly, no outcomes relevant to wandering were measured in any of them. It is important also to note that the hallmark of onset in the paradigmatic cortical dementia, AD, is the failure of semantic memory, which cannot be measured in any animal model and so all animal models share this deficiency as well. For example, Hamano et al., 2019, administered 12 mg/kg/day (68 mg HED) to rTG4510 tau transgenic mice and measured only tau phosphorylation/cleavage and oligomers, but no outcomes. Elliott 2018 used a triple transgenic mouse model (APP Swedish, MAPT P301L, and PSEN1 M146V) and observed reduce ß-amyloid plaques in vivo at a dose of 10 mg/kg/day (intraperitoneally) fasudil (57 mg HED). Sellers 2018 used the AB42 mouse model and administered fasudil intraperitoneally at a dose of 10 mg/kg BID (226 mg HED) but monitored only ß-amyloid dendritic spine loss. Couch et al. 2010 used intraventricular infusion and observed effects on dendritic branching and no outcomes relevant to wandering. Putting aside the absence of any behavioral outcomes in these references, intraventricular administration is not a therapeutic option for humans. Yu 2017 and Hou 2012 administered fasudil at 5 and 10 mg/kg/day intraperitoneally to APP/PS1 transgenic mice (70, 140 mg HED) and streptozotocin rats (226 mg HED), respectively and observed that latency distance and quadrant time were improved in the Morris water maze (a model for spatial learning and memory, not wandering). There is no clear link between memory loss and wandering as not all patients with cortical dementia wander.

Conflicting reports to the above also exist. For example, Turk 2018 (dissertation) used triple transgenic mice and did not observe improvements in spatial memory at 10 or 12 months of age with fasudil administered in water at 30 mg/kg and 100 mg/kg.

Based on currently available animal modeling, different therapeutic strategies targeting the pathological hallmarks of dementia have been tested but have failed to show any beneficial effects in humans. At present, available medications are limited to acetylcholinesterase inhibitors and N-methyl-D-aspartate (NMDA) receptor antagonists, which show only modest improvements in some cognitive symptoms. No existing or even proposed therapies address the problem of wandering in dementia, which is not treated by the foregoing approved therapeutics. There exists a significant unmet need to provide new therapies that show benefit in humans, not just animals.

SUMMARY OF THE INVENTION

One embodiment of the invention involves a method of treating a patient with wandering due to cortical dementia, comprising treating said patient with a therapeutically effective amount of fasudil. In certain aspects of this embodiment, the dementia is multi-infarct dementia, caused by ischemia and/or not caused by hemorrhage. In certain aspects of this embodiment, the patient does not have sub-cortical dementia. In another embodiment, the patient has mixed dementia (vascular dementia associated with proteinopathy-associated dementia). In another embodiment, the patient does not have mixed dementia. In a specific embodiment, the patient is female. In another specific embodiment, the patient has early-onset dementia. In yet a further specific embodiment, the patient has Down's syndrome-associated dementia. In a further embodiment, the patient has Korsakoff syndrome. In another specific embodiment, the patient to be treated has at least one ApoE ε4 allele.

A preferred aspect of the invention contemplates a method of treating a patient with wandering due to cortical vascular dementia, comprising treating said patient with a therapeutically effective amount of fasudil. In certain aspects of this embodiment, the dementia is multi-infarct dementia, caused by ischemia and/or not caused by hemorrhage.

Other embodiments relate to treating a patient with wandering due to vascular dementia that is not Binswanger's disease or lacunar dementia, comprising treating said patient with a therapeutically effective amount of fasudil. In another embodiment, the patient treated for wandering associated with cortical dementia does not exhibit pseudobulbar affect, or does not manifest emotional incontinence including but not limited to compulsive or inappropriate laughing and/or crying.

In a certain preferred embodiment, the inventive methods include method of treating a patient with wandering due to dementia, comprising treating said patient with a therapeutically effective amount of fasudil, where said patient has not previously been treated with fasudil for chronic stroke.

Still another aspect of the invention includes a method of treating a patient with wandering due to dementia, wherein the patient does not display a wayfinding defect, comprising treating said patient with a therapeutically effective amount of fasudil.

Another preferred embodiment involves a method of treating a patient with wandering due dementia, wherein the patient engages in elopement, escape or boundary transgressions, comprising treating said patient with a therapeutically effective amount of fasudil. According to this embodiment the patient may be a sporadic or persistent wanderer.

Yet another embodiment includes a method of treating a patient with wandering dementia, wherein the patient is a persistent wanderer who is in motion at least 20% of waking hours, comprising treating said patient with a therapeutically effective amount of fasudil.

In a further embodiment, the invention includes a method of treating a patient wherein progression from wayfinding defects to elopement, escape or boundary transgressions is delayed or prevented upon treatment with fasudil.

In another embodiment the invention includes a method of treating a patient for wandering, wherein the treatment eliminates use of chemical restraints such as use of antipsychotic medications (e.g., aripiprazole, clozapine, haloperidol, olanzapine, quetiapine, risperidone and ziprasidone).

In another embodiment, the patient to be treated for wandering has been placed into an unfamiliar environment, such as removed from home into a care facility. In a specific embodiment, treatment with fasudil reduces intrusion into the room of a co-resident in a care facility.

In a further embodiment, the patient to be treated has recently undergone a change in medication including neuroleptic medications, especially those that induce akathisia.

In another embodiment, the patent to be treated for wandering has a history of depression, anxiety, or schizophrenia.

DETAILED DESCRIPTION OF THE INVENTION

The invention is based on the discovery that rho kinase inhibitors can be used to treat wandering in dementia patients where the dementia is cortical, rather than subcortical. Multi-infarct dementia is considered to be a type of cortical dementia, even though there may be subcortical involvement. A preferred embodiment of the invention contemplates the treatment of wandering in cortical vascular dementia. Another aspect of the invention contemplates the treatment of wandering in dementia patients who are persistent wanderers who are in motion an excessive amount of their waking time. An additional important aspect of the invention involves treating wandering in dementia patients who do not display a wayfinding defect.

ROCK Inhibitors

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A large number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinolone derived ROCK inhibitors include dimethylfasudil and ripasudil.

Other preferred ROCK inhibitors are based on based on 4-aminopyridine structures. These were first developed by Yoshitomi Pharmaceutical (Uehata et al., 1997) and are exemplified by Y-27632. Still other preferred ROCK inhibitors include indazole, pyrimidine, pyrrolopyridine, pyrazole, benzimidazole, benzothiazole, benzathiophene, benzamide, aminofurazane, quinazoline, and boron derivatives (Feng et al., 2015). Some exemplary ROCK inhibitors are shown below:

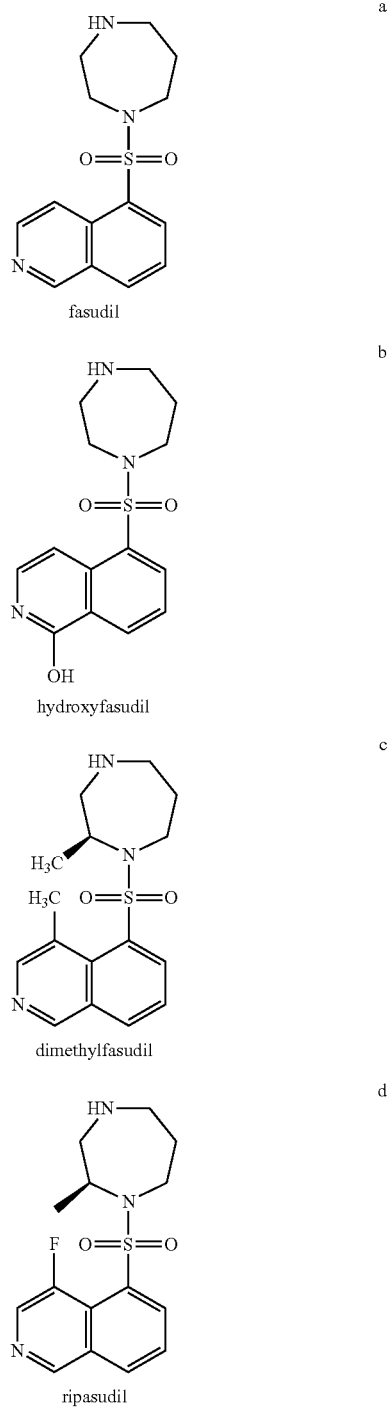

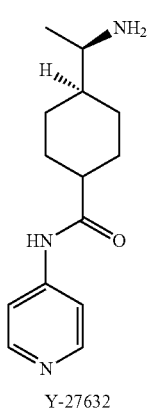

Y-27632

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 or ROCK2 and have much lower activity against PKA, PKG, PKC, and MLCK.

A particularly preferred ROCK inhibitor is fasudil. Fasudil may exist as a free base or salt and may be in the form of a hydrate, such as a hemihydrate. As used herein, it will be understood that methods specifying the active moiety of a ROCK inhibitor apply equally to the free acids or free bases, salts, hydrates, polymorphs and prodrug derivatives thereof

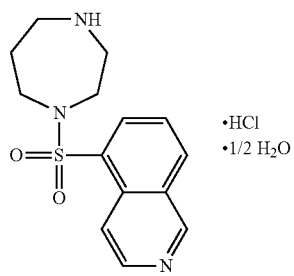 [SMILES: O=S(=O)(c1cccc2cnccc12)N1CCCNCC1]

Hexahydro-1-(5-isoquinolinesulfonyl)-1H-1,4-diazepine monohydrochloride hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule. M3 exists as two tautomers, depicted below:

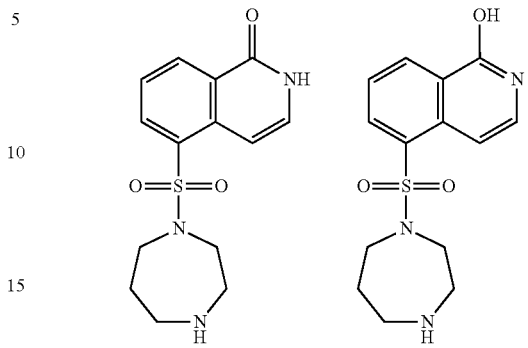

The ROCK inhibitors used in the invention, such as fasudil, include pharmaceutically acceptable salts and hydrates. Salts that may be formed via reaction with inorganic and organic acid. Those inorganic and organic acids are included as following: hydrochloric acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

Pharmaceutical Compositions

Pharmaceutical compositions of ROCK inhibitors usable in the invention are generally oral and may be in the form of tablets or capsules and may be immediate-release formulations or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug—using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Certain patients with dementia exhibit dysphagia and may need formulations such as semisolid dosage forms (gels and jellies), orally disintegrating tablets, or sublingual dosage forms.

Methods of Treatment

Dementia broadly results from damage to one of two areas of the brain: the cortex (aka, the cerebral cortex) and the subcortex. The differentiation between cortical (of the cortex) and subcortical (of the subcortex) forms of dementia can often be done by observing the deficits and relating them back to the brain structures associated with that function.

The subcortex consists of three main divisions. The first is the basal ganglia, which is involved in motor control and skills learning. Defects in this area cause either hypokinetic or hyperkinetic problems. Parkinson's and Huntington's disease affect the basal ganglia. The second is the limbic system, which primarily functions in the detection and expression of emotion. It consists of the amygdala, which detects fearful or threatening objects, and the hippocampus, which is involved in laughter. The connection between the amygdala, thalamus (part of the diencephalon) and hippocampus is associated with positive feelings. The hippocampus also plays an important role in learning, memory and detecting novelty. The third is the diencephalon, which consists of the thalamus and hypothalamus. The thalamus is the main sensory relay for all senses, except smell, between the sense organs. The hypothalamus regulates body temperature, hunger, sexual behavior and thirst.

The cerebral cortex is the outermost layer of the cerebrum. It is made up of four lobes and is involved in complex brain functions including memory, attention, perceptual awareness, "thinking," language and consciousness. It also controls voluntary motor function. Thus, the cortex is often described functionally, in terms of its primary sensory and motor areas.

The parietal, temporal and occipital lobes are involved in producing our perceptions resulting from what our eyes see, ears hear and other sensory organs tell us about the position of different parts of our body and relate them to the position of other objects in the environment. The parietal-temporal-occipital complex, especially of the left hemisphere, is responsible for our understanding and use of language. The frontal lobe is involved in planning actions and movement, as well as abstract thought. The limbic area is involved in emotion and memory The motor areas are located in both hemispheres of the cortex. The primary motor cortex controls executing voluntary movements. The supplementary motor areas and premotor cortex are involved in selecting voluntary movements. The posterior parietal cortex guides voluntary movements in space. The dorsolateral prefrontal cortex is involved in deciding which voluntary movements to make according to higher-order instructions, rules and self-generated thoughts.

The following table illustrates some broad difference between the defects found in cortical versus subcortical forms of dementia.

| Cortical | Subcortical |
|---|---|
| General lack of motor symptoms | Motor symptoms common |
| No coordination defect | Lack of coordination |
| Normal cognitive processing, wrong answers | Slow, but correct answers |
| Severe amnesia, recall and recognition affected | Better recognition, improved by clues |
| Unable to calculate | Able to calculate |
| Executive abilities preserved | Executive abilities disproportionately affected |
| Aphasia prominent | Normal with dysarthria and less word output |
| Personality intact until late | Apathetic and inert |

Examples of cortical dementia are Alzheimer's (AD), Vascular Dementia, Lewy Body (LBD), Frontotemporal Lobar (FTD; Pick's Disease), Frontotemporal Lobar (FTD; Primary Progressive Aphasia (PPA))

Examples of subcortical dementia are Binswanger's disease (BD; lacunar dementia), Parkinson's Disease (PD), Huntington's Disease (HD) and Multiple Sclerosis (MS).

Just as dementia is not a single condition, the wandering that results from the various underlying forms of dementia clearly is not a single condition. Wandering is not a simple function of cognitive decline. In fact, while cognitive impairment is correlated with frequency of wandering cycles, it is not correlated with the other domains of wandering (Algase 2001b). Several lines of evidence demonstrate that wandering is a reflection of the specific underlying pathology of the type, or even sub-type, of dementia.

First, wandering is more prevalent in certain types of dementia than others. Cooper (1993) found in a study of 1312 dementia patients that wandering occurred in 26% of AD patients versus 17% in VaD, the difference reaching statistical significance, and that while the severity of wandering is associated with progression of dementia, the higher prevalence of wandering in AD versus VaD was consistent among early-, mid- and late-stages of disease. Confirming the difference in wandering rate among different forms of dementia, in a study of 638 community-residing dementia patients, Klein (1999) observed wandering in 14.1% of VaD patients and 21.4% in AD. Knuffman (2001) found that wandering was much more common in DLB than in AD.

Second, differences in wandering patterns in different forms of dementia indicate grounding in different pathologies. Routinized wandering, like repetitive pacing and lapping, is very common in FTD and rare in AD, in which wandering tends to be unpatterned; patterned wandering in VaD is even more rare than in either AD or FTD (Bathgate 2001). Repetitive pacing and lapping, evolving to a fixed route in advanced disease, are strongly predictive of FTD and can be used to help distinguish FTD from AD (Nakaoka 2010). Moreover, AD patients get lost outside of their homes at a much higher rate than VaD patients (41% versus 20%) (Ballard 1991). Even between forms of AD, patterns can differ. Nakaoka (2010) observed that excessive (>10 km per day), non-patterned wandering was limited to early-onset AD patients with significant levels of cognitive impairment.

Wandering generally can be characterized by two domains. The first domain is movement, generally in the form of ambulation unless the patient is disabled and, for example, confined to a wheelchair. The second domain is problematic behavior, usually in the form of boundary transgressions and/or wayfinding problems. However, it could be reflected in the movement itself, such as pacing or lapping behavior. It may involve inappropriately following a caregiver. A common problematic behavior is attempted escape or elopement. A certain quantity of movement may also be considered the problematic behavior. A normal person is in motion approximately 10% of their waking hours and so movement beyond this threshold amount can be considered problematic behavior. A patient will be considered to suffer from wandering when in motion for at least 20% of their waking hours, but preferably more than 30% of their waking hours. As a patient spends more time in motion, the behavior becomes particularly problematic because they risk exhaustion and, therefore, falling and serious injury. Thus, some wandering patients are in motion more that 40% or 50% of their waking hours and some more than 60%, 70% or even 80%.

It has been proposed that wandering can be persistent or sporadic and the present methods may be used to treat either population. Persistent wanderers exhibit excessive movement nearly every day, typically at least 4-5 days per week. On the other hand, sporadic wanderers do not exhibit excessive movement, but rather they are generally sedentary with occasional movement, typically associated with elopement, boundary transgressions, escape or wayfinding defects. Sporadic wanders may exhibit the behavior as infrequently as monthly or as frequently as 2, 3 or even 4, 5, 6, or more times per week. Unlike the persistent wanderer, the sporadic wonderer does not spend an abnormally high amount of time in motion. In one preferred embodiment of the invention, patients treated wander due to dementia of any form and do not display a wayfinding defect; such a patient may be a persistent or a sporadic wanderer.

In one specific embodiment, treatment with fasudil reduces the amount of repetitive movement wandering (e.g., lapping, pacing) in the patients by at least 10%; 15%; 20%; 25%; 30%; 35%; 40%; 45% or 50%. In another embodiment, treatment with fasudil reduces the amount repetitive movement wandering by 50% or more. In preferred embodiments, treatment with fasudil reduces repetitive movement by at least 75%. In a preferred embodiment, treatment with fasudil reduces the amount of repetitive movement wandering to the normative 10% motion during waking hours.

In a further embodiment, treatment with fasudil reduces the number of times per day repetitive movement wandering occurs by at least one time, preferably by at least two times, and more preferably by at least three times per day.

In a further embodiment, treatment with fasudil reduces the number of days repetitive movement wandering occurs by at least one day per week, preferably by at least two days per week, and more preferably by at least three days per week.

In another specific embodiments, treatment with fasudil reduces persistent wandering by at least 10%; 15%; 20%; 25%; 30%; 35%; 40%; 45% or 50%. In another embodiment, treatment with fasudil reduces persistent wandering by 50% or more. In preferred embodiments, treatment with fasudil hydrochloride hemihydrate reduces persistent wandering by at least 75%. In a preferred embodiment, treatment with fasudil reduces persistent wandering to the normative 10% motion during waking hours.

In a further embodiment, treatment with fasudil reduces the number of days wandering occurs in persistent wandering by at least one day per week, preferably by at least two days per week, and more preferably by at least three days per week.

In another embodiment, treatment with fasudil reduces sporadic wandering by at least 10%; 15%; 20%; 25%; 30%; 35%; 40%; 45% or 50%. In another embodiment, treatment with fasudil reduces sporadic wandering by 50% or more. In preferred embodiments, treatment with fasudil reduces sporadic wandering by at least 75%. In a preferred embodiment, treatment with fasudil reduces sporadic wandering to the normative 10% motion during waking hours.

In another embodiment, treatment with fasudil reduces pacing or lapping by at least 10%; 15%; 20%; 25%; 30%; 35%; 40%; 45% or 50%. In another embodiment, treatment with fasudil reduces pacing or lapping by 50% or more. In preferred embodiments, treatment with fasudil reduces pacing or lapping by at least 75%.

In another embodiment, treatment with fasudil reduces eloping behavior by at least 10%; 15%; 20%; 25%; 30%; 35%; 40%; 45% or 50%. In another embodiment, treatment with fasudil reduces eloping behavior by 50% or more. In preferred embodiments, treatment with fasudil reduces eloping behavior by at least 75%.

In another embodiment, treatment with fasudil reduces spatial disorientation by at least 10%; 15%; 20%; 25%; 30%; 35%; 40%; 45% or 50%. In another embodiment, treatment with fasudil reduces spatial disorientation by 50% or more. In preferred embodiments, treatment with fasudil reduces spatial disorientation by at least 75%.

In another embodiment, treatment with fasudil reduces the caregiver burden associated with wandering by at least 10%; 15%; 20%; 25%; 30%; 35%; 40%; 45% or 50%. In another embodiment, treatment with fasudil reduces the caregiver burden associated with wandering by 50% or more. In preferred embodiments, treatment with fasudil reduces the caregiver burden associated with wandering by at least 75%.

In another embodiment, treatment with fasudil reduces the caregiver burden associated with one or more of persistent wandering, pacing, elopement and spatial disorientation by at least 10%; 15%; 20%; 25%; 30%; 35%; 40%; 45% or 50%. In another embodiment, treatment with fasudil reduces the caregiver burden associated with one or more of persistent wandering, pacing, elopement and spatial disorientation by 50% or more. In preferred embodiments, treatment with fasudil reduces the caregiver burden associated with one or more of persistent wandering, pacing, elopement and spatial disorientation by at least 75%.

In a further embodiment, treatment with fasudil reduces the number of days wandering occurs in sporadic wandering by at least one day per week, preferably by at least two days per week, and more preferably by at least three days per week.

In another embodiment, treatment with fasudil reduces the wandering occurs during sundowning, or early evening. In another embodiment, treatment with fasudil reduces the wandering occurs during the overnight hours. In one embodiment, the amount of wandering to determine the reduction can be measured using electronic motion and/or activity tracking device, including fitness trackers such as Fitbits. The fitness trackers can be used alone or in combination with GPS devices to measure location.

The Revised Algase Wandering Scale (Long Term Care Version) is a preferred instrument for measuring wandering (Nelson and Algase 2006). It is divided into three different domains based on the three main wandering typologies: Persistent Wandering (PW); Eloping Behavior (EB); and Spatial Disorientation (SD). Each domain evaluates individual items on a scale that can be quantified with a score from 1-4.

An overall domain score is calculated based on the number of questions with a valid response. Thus, the individual scores are added up and divided by the number of questions in the domain with valid responses. It is highly preferred that at least 75% of the items in a domain have valid responses. The result will be a score from 1 to 4.

Likewise, an overall scale score may be obtained by averaging each of the 3 domains, resulting in a global score of 1-4. Alternatively, for the highest level of granularity, each individual item within a domain may be assessed individually.

The RAWS can be filled out by staff or a caregiver.

The PW domain consists of 9 individual items that look at the amount of spontaneous walking in absolute terms and relative to other similarly situated patients, pacing and restless walking (which may indicate agitation) and the timing of the wandering relative to mealtimes, which may be indicative of provocation to wander.

The EB domain consists of 4 items. It measures running off, entering unauthorized areas, leaving authorized areas and returns to authorized areas after an unnoticed leaving.

The SD domain consists of 6 items that assess getting lost, aimless walking, running into people and objects and the inability to locate certain rooms.

In certain embodiments, patients treated according to the invention will show improvements in at least 1 item of the RAWS. In preferred embodiments, patients will show improvements in at least one domain of the RAWS. In particularly preferred embodiments, patients will show improvements in the PW and/or the EB domain of the RAWS. Such improvements will generally be in the range of 10%; 15%; 20%; 25%; 30%; 35%; 40%; 45% or 50%.

REVISED ALGASE WANDERING SCALE

PERSISTENT WALKING (PW)

1. Resident has a reduced amount of spontaneous walking
   walks the same or more as others of the same age and ability
   walks less than others of same age and ability
   walks only minimally, e.g. to go to bathroom
   does not walk spontaneously unless prompted

REVISED ALGASE WANDERING SCALE

2. Resident has an increased amount of spontaneous walking
   walks about the same as others of same age and ability
   walks distinctly more than average, but will sit for periods
   walks distinctly more than average, rarely sits
   walks distinctly more than average, never sits
3. Resident walks about on their own
   only if prompted
   occasionally during the day
   frequently during the day
   almost constantly during the day
4. Resident walks around restlessly
   never
   on a few occasions
   regularly but not daily
   on a daily basis
5. Resident paces up and down
   never
   on a few occasions
   regularly but not daily
   on a daily basis
6. Resident walks around after awakening but before breakfast
   never
   less than others of same age and ability
   the same as others of the same age and ability
   more than others of same age and ability
7. Residents walks around between breakfast and lunch
   never
   less than others of same age and ability
   the same as others of the same age and ability
   more than others of same age and ability
8. Resident walks around between lunch and dinner
   never
   less than others of same age and ability
   the same as others of the same age and ability
   more than others of same age and ability
9. Resident walks around after dinner but before bedtime
   never
   less than others of same age and ability
   the same as others of the same age and ability
   more than others of same age and ability

ELOPING BEHAVIOUR (EB)

10. Resident attempts to leave their authorised area
    never
    on a few occasions
    regularly but not daily
    on a daily basis
11. Resident runs off
    never
    on a few occasions
    regularly but not daily
    on a daily basis
12. Resident enters unauthorised areas
    never
    on a few occasions
    regularly but not daily
    on a daily basis
13. Resident was returned to authorised area after leaving unnoticed
    never
    only once
    more than once, but not often
    often

SPATIAL DISORIENTIATION (SD)

14. Resident gets lost
    never
    on a few occasions
    regularly but not daily
    on a daily basis
15. Resident cannot locate bathroom without help
    requires no help
    sometimes requires help
    usually requires help
    always required help

| REVISED ALGASE WANDERING SCALE |
| --- |
| 16. Resident cannot locate dining room without help<br>   requires no help<br>   sometimes requires help<br>   usually requires help<br>   always required help<br>17. Resident cannot locate own room without help<br>   requires no help<br>   sometimes requires help<br>   usually requires help<br>   always required help<br>18. Resident walks about aimlessly<br>   always has an identifiable destination/goal<br>   usually has an identifiable destination/goal<br>   sometimes has an identifiable destination/goal<br>   never has an identifiable destination/goal<br>19. Whilst walking alone, resident bumps into obstacles or other people<br>   never<br>   on a few occasions<br>   regularly but not daily<br>   on a daily basis |

Another useful measuring tool for wandering is the Woolsey Wandering Questionnaire (WWQ), presented below. A significant feature of the WWQ is that it also captures the burden of wandering behavior on the caregiver. This burden is assessed overall as a global impression and also with respect to each domain. It is administered weekly. Question 1 is a global impression of burden. Question 2 looks specifically at persistent or spontaneous wandering. Question 3 looks specifically elopement. Question 4 looks at pacing, a type of spontaneous walking that may be associated with agitation. Question 5 relates to spatial disorientation.

Each response is assigned a numerical value, with more problematic behavior (first response) assigned the higher score. Thus, question 1 would be scored, for example, 4 for very problematic behavior and 1 for no wandering observed. Question 2 would be scored on a 5-point scale, with above average walking with no sitting being assigned a 5, and walking distinctly less than average being assigned a 1. In this way, each question can be assessed separately, or the tool may be assessed globally. The global assessment can be in terms of an overall score (all questions) or a burden score (only caregiver burden questions) or a wandering score (only the behavioral portions of questions 2-5).

| Woolsey Wandering Questionnaire |
| --- |
| 1. OVERALL, if wandering was observed, how problematic was the resident's wandering behavior this week?<br>   Very problematic<br>   Problematic<br>   Not problematic<br>   No wandering was observed<br>2. Relative to other residents of similar abilities this week, the subject (Purpose of question: assesses persistent wandering or wandering frequency) walked distinctly more than average and<br>     never sat<br>     rarely sat<br>     sat for periods<br>did not walk distinctly more than average<br>     walked an average amount<br>     walked distinctly less than average<br>2a) If resident walked more than average, how frequently? (Purpose of question: assess wandering frequency)<br>   On a daily basis<br>   Regularly but not daily<br>   On a few occasions<br>   N/A, resident did not walk more than average |

| Woolsey Wandering Questionnaire |
| --- |
| 2b) How problematic was this behavior to you as a caregiver or staff?<br>   Very problematic<br>   Problematic<br>   Not problematic<br>3. How many times did the resident attempt to leave authorized areas or enter unauthorized areas? (Purpose of question: assesses elopement)<br>   More than twice (Estimated number of times: ____)<br>   Twice<br>   Once<br>   None<br>3a.) How problematic was this behavior to you as a caregiver or staff?<br>   Very problematic<br>   Problematic<br>   Not problematic<br>4. Was the resident observed pacing, as evidenced by repetitively walking back and forth? (Purpose of question: pacing may suggest agitation)<br>   On a daily basis<br>   Regularly but not daily<br>   On a few occasions<br>   Not at all<br>4a) How problematic was this behavior to you as a caregiver or staff?<br>   Very problematic<br>   Problematic<br>   Not problematic<br>5. Did the resident get lost? (Purpose of question: assesses wayfinding and/or spatial disorientation)<br>   On a daily basis<br>   Regularly but not daily<br>   On a few occasions<br>   Not at all<br>5a) How problematic was this behavior to you as a caregiver or staff?<br>   Very problematic<br>   Problematic<br>   Not problematic |

In accordance with the treatment methods of the present invention, an effective amount of a ROCK inhibitor or a pharmaceutically acceptable salt thereof for administration one or more times a day may comprise from about 10 mg to about 1000 mg. Fasudil hydrochloride hemihydrate, for example, is suitably administered in a daily amount of about 10 mg to about 500 mg, about 10 mg to about 400 mg, about 10 mg to about 200 mg, about 10 mg to about 100 mg, about 20 mg to about 10 mg. One preferred dosing regimen involves the treatment with 25, 30 or 40 mg of Fasudil hydrochloride hemihydrate three times per day using an immediate-release formulation, for a total daily dose of 75-120 mg. Most preferred dosing exceeds a daily dose of 60 mg, with most preferred ranges for daily dosing being 70 mg to 120 mg administered in three equal amounts during the day. A particularly preferred daily dose is 90 mg per day. A further dosing regimen involves the treatment with, 35 to 60 mg of Fasudil hydrochloride hemihydrate only two times per day using an immediate-release formulation, for a total daily dose of 70-120 mg. A preferred embodiment is 45 mg of fasudil hydrochloride hemihydrate two times per day using an immediate-release formulation. The ROCK inhibitors according to the invention are most preferably administered orally in accordance with the foregoing using an immediate release formulation.

Certain patient sub-populations, such as renally impaired patients and/or older patients (e.g., 65 or older) may need lower doses or extended release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

Renal dysfunction occurs with age and as the result of numerous disorders, including liver cirrhosis, chronic kidney disease, acute kidney injury (for example, due to administering a contrast agent), diabetes (Type 1 or Type 2), autoimmune diseases (such as lupus and IgA nephropathy), genetic diseases (such as polycystic kidney disease), nephrotic syndrome, urinary tract problems (from conditions such as enlarged prostate, kidney stones and some cancers), heart attack, illegal drug use and drug abuse, ischemic kidney conditions, urinary tract problems, high blood pressure, glomerulonephritis, interstitial nephritis, vesicoureteral, pyelonephritis, sepsis. Kidney dysfunction may occur in other diseases and syndromes, including non-kidney-related diseases that may occur along with kidney dysfunction, for example pulmonary artery hypertension, heart failure, and cardiomyopathies, among others.

Kidney function is most often assessed using serum (and/or urine) creatinine. Creatinine is a breakdown product of creatine phosphate in muscle cells and it is produced at a constant rate. It is excreted by the kidneys unchanged, principally through glomerular filtration. Accordingly, elevated serum creatinine is a marker for kidney dysfunction and it is used to estimate glomerular filtration rate.

Normal levels of creatinine in the blood are approximately 0.6 to 1.2 mg/dL in adult males and 0.5 to 1.1 mg/dL in adult females. When creatinine levels exceed these figures, the subject has renal dysfunction, and is, therefore, treatable according to the invention. Mild renal impairment/dysfunction occurs in the range of 1.2 mg/dL to 1.5 mg/dL. Moderate renal impairment/dysfunction is considered to occur at creatinine levels exceeding 1.5 mg/dL. Severe renal impairment, which includes what is considered to be renal failure, is defined as a serum creatinine level of $\geq 2.0$ mg/dL or the use of renal replacement therapy (such as dialysis). Treating subjects with mild, moderate and severe renal impairment is specifically contemplated.

As indicated, creatinine levels are considered to be a surrogate for glomerular filtration rate and serum creatinine levels alone may be used to estimate glomerular filtration rate using the Cockroft-Gault equation.

Generally, creatinine clearance of less than 60 mL/min (corresponding roughly to creatinine of >1.2 mg/dL) is considered moderate renal dysfunction. A glomerular filtration rate below 40 mL/min (corresponding approximately to creatinine levels exceeding 1.5 mg/dL) or especially 30 mL/min is considered severe renal dysfunction.

In general, creatinine clearance (estimated glomerular filtration rate) may be derived directly from serum creatinine using the Cockroft-Gault equation:

creatinine clearance=(((140−age in years)×(wt in kg))×1.23)/(serum creatinine in μmol/L)

For women the result of the calculation is multiplied by 0.85.

Empirically measured creatinine clearance may also be used directly as an estimate of glomerular filtration rate by looking at serum creatinine and urine creatinine levels. Specifically, urine is collected over 24 hours and the following equation is applied to ascertain creatinine clearance:

Creatinine Clearance (mL/min)=Urine Creatinine Concentration (mg/mL)*24 hour urine volume (mL)/Plasma Creatinine Concentration (mg/mL) *24 hour*60 minutes In one embodiment, dose of fasudil for mild to moderate renal impairment is reduced to 50-80 mg per day. In another embodiment, the dose of fasudil is not reduced but is administered one time per day in an extended release dosage form.

In another embodiment, the dose is not reduced for mild to moderate renal impairment.

In one embodiment, the dose of fasudil is reduced to 30-45 for severe renal impairment. In another embodiment, the dose of fasudil is not reduced but is instead administered one time per day in an extended release dosage form.

In a further embodiment, the dose is reduced where serum creatinine (SCr)>2 and/or an increase in SCr>1.5× from baseline, and/or a decrease in eGFR>25% from baseline.

Patient size is an important factor to consider when using creatinine-based estimates of renal function. The units of drug clearance are volume/time (mL/min), whereas the units of estimated GFR for chronic renal disease are volume/time/standard size (mL/min/1.73 m$^2$). Generally, doses may be adjusted down (e.g., 40-50 mg per day) for smaller patients and up for larger (e.g., 120 mg per day) for obese patients. A smaller male would be about 160 pounds or less. A smaller female patient would weigh about 130 pounds or less. Patients having a Body Mass Index of 30 and higher is considered obese.

In addition, older patients may need a lower dose at initiation, with a gradual increase to the recommended dose after days or weeks. In another embodiment, older patients may need lower doses for the duration of treatment. The aged population includes the "young old" who are 65-74, the "old old" who are 75-84 and the "frail elderly" who are 85 and older. For example, a starting dose of 30 mg per day for two weeks, followed by 60 mg per day for 4 weeks, then by 90 mg per day. Titration may even be warranted up to about 120 mg per day.

Another embodiment involves the treatment with 60-120 mg of fasudil hydrochloride hemihydrate once per day in an extended release dosage form. Treatment with an extended release total daily dose of 90 mg fasudil hydrochloride hemihydrate once per day is preferred. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment.

Patients treatable according to the invention will typically score poorly on cognitive scales, such as the mini mental state exam (MMSE). A threshold of ≤23 on the MMSE is set for dementia, with score of ≤15 representing severe dementia. Thus, the invention particularly contemplates treating patients with an MMSE score≤23, including moderately demented patients having an MMSE score of 16-23 and severe patients having an MMSE score≤15. Generally, once a patient has an MMSE score of less than 9, they may develop problems walking and treatment of patients with an MMSE less than 5 is not preferred. Once the MMSE falls below 15, the Severe Impairment Battery (SIB) is a useful assessment too. Treatment using the inventive methods generally result in improved cognitive functioning. Patients will generally show improvement on the MMSE and the SIB of at least 3 points during the early stages of treatment and declines in cognition are slowed relative to control patients.

The MMSE, is described fully in Folstein (1975, 1987 and 2007). Generally, an MMSE score of 24-30 indicates no cognitive impairment, a score of 18-23 indicates mild cognitive impairment and 0-17 indicates severe cognitive impairment.

The methods of the invention also contemplate administering ROCK inhibitors with other compounds used to treat dementia or other symptoms of dementia. They may be administered in combination, a single dosage form, in a common dosing regimen or administered to the same patient at different times of the day using different dosing regiments.

In some embodiments, the patients are administered fasudil in combination with other actives approved to treat cortical dementia, including but not limited to cholinesterase inhibitors and NMDA receptor antagonists. In one embodiment, the cholinesterase inhibitor is selected from the group consisting of donepezil, rivastigmine, and galantamine. Exemplary doses of the cholinesterase inhibitors include 3-25 mg per day, more preferably 6-12 mg per day. In another embodiment, the NMDA receptor antagonist is memantine. In a specific embodiment, memantine is administered at a dose of 5-28 mg per day, preferably 15-20 mg per day. In a further embodiment, the co-administered active is a combination of donepezil and memantine at a dose of 28 mg memantine and 10 mg donepezil.

In a specific embodiment, the combination of fasudil with cholinesterase inhibitors is administered to wandering patients with proteinopathy-associated cortical dementia. In a further embodiment, the combination of fasudil with cholinesterase inhibitors is administered to wandering patients with mixed dementia. In yet a further embodiment, the combination of fasudil with cholinesterase inhibitors is not administered to wandering patients with only vascular cortical dementia.

Dextromethorphan hydrobromide is another an uncompetitive NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which occurs in many forms of dementia.

In a further embodiment, the patient treated with fasudil is not also being treated with active agents including mood stabilizers, benzodiazepines, antipsychotics, anti-agitation drugs, or sleep aids. In a specific embodiment, the patient treated with fasudil is not being treated with risperidone, ariprprazole, quetiapine, carbamazepine, gabapentin, prazocin, trazodone or lorazepam.

In a further embodiment the patient treated with fasudil is being treated for depression. In a specific embodiment, the patient is treated with an anti-depressant such as citalopram or escitalopram.

Example 1

A clinical trial is conducted in order to determine the effectiveness of oral fasudil in reducing the frequency of wandering in patients with Alzheimer's Dementia (AD) and cortical vascular dementia (VaD).

Twenty patients, 10 with AD and 10 with VaD (confirmed by MM) who are characterized wanderers, are enrolled into the study and observed for 2 weeks to confirm wandering behavior. Confirmed wanderers receive fasudil in an open-label run in period for 6 weeks at 90 mg/day (30 mg TID) to evaluate any effect on wandering and then enter the double-blind phase where they receive test drug 90 mg/day (30 mg TID) or matching placebo (TID) for 6 weeks. The double-blind phase is followed by another treatment period of 6 weeks with the opposite treatment assignment (placebo or test drug taken with food).

The following inclusion criteria are applied:
1. Patients 50 years to 90 years of age.
2. Diagnosis of dementia (AD or VaD or mixed type) for at least 6 months.
3. For entering observation period and for entering open label treatment period:
Wanders:
   a. Walks distinctly more than average as others of same age and ability AND/OR
   b. Elopement behavior≥3× per week in the opinion of the investigator Criteria for Entering First Double-Blind Treatment Period:
Wanders:
   a. Walks less than half the mean distance measured in observation period AND/OR
   b. Elopement behavior<1× per week in the opinion of the investigator AND/OR
   c. Wandering has improved in the opinion of the Investigator.

4. For entering observation period and for entering open label treatment period:
   a. MMSE between 10 and 25.

Wandering is measured in term of time in motion and distance traveled (measures of persistent wandering), attempted and successful boundary transgressions (measures of elopement) and patterns like pacing a lapping (indicative of persistent wandering and/or agitation or anxiety) using an electronic tracking device. A typical tracking device would use a combination of accelerometry with positioning, using technology like RFID or Bluetooth in an indoor environment and GPS outdoors. Other wayfinding, orientation and memory-associated wandering incidents are observed and recorded manually.

The Mini Mental State Exam (MMSE), the Woolsey Wandering Questionnaire and the Revised Algase Wandering Scale are administered at baseline and at the end of each treatment period. Any change in the use of antipsychotics or anxiolytics that could affect movement during the study is strongly discouraged.

Treatment with fasudil is associated with a significant reduction in wandering at least one item of the RAWS and/or the WWQ. Persistent wanderers reduce activity levels by about 50% while on drug as compared to placebo and this is accompanied by a mean increase in MMSE score of greater than 3 points. Sporadic wanderers show a significant reduction in wayfinding errors and other problematic behaviors while on drug, with a similar improvement in MMSE. Measures of caregiver burden also show a significant effect, indicating wandering becomes less problematic.

LIST OF REFERENCES

Algase D L, Beattie E R, Bogue E L, Yao L. 2001a. The Algase Wandering Scale: initial psychometrics of a new caregiver reporting tool. Am J Alzheimers Dis Other Demen. 16:141-152.

Algase D L, Beattie E R, Therrien B. 2001b. Impact of cognitive impairment on wandering behavior. West J Nurs Res. 23:283-95.

Aud M A. Dangerous wandering: elopements of older adults with dementia from long-term care facilities. Am J Alzheimers Dis Other Demen. 2004; 19(6):361-368.

Ballard C G, Mohan R N C, Bannister C, Handy S, Patel A. 1991. Wandering in Dementia Sufferers. Int J Geriatr Psych 6:611-614.

Bathgate D, Snowden J S, Varma A, et al. 2001. Behaviour in frontotemporal dementia, Alzheimer's disease and vascular dementia. Acta Neurol Scand. 103:367-378.

Ceyzériat K, et al., Learning from the Past: A Review of Clinical Trials Targeting Amyloid, Tau and Neuroinflammation in Alzheimer's Disease. Current Alzheimer Research. 2020; 17: 1-13.

Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.

Cipriani G, Lucetti C, Nuti A, Danti S. 2014. Wandering and dementia. Psychogeriatrics. 14:135-42.

Cooper J K, Mungas D. 1993. Risk factor and behavioral differences between vascular and Alzheimer's dementias: the pathway to end-stage disease. J Geriatr Psychiatry Neurol. 6:29-33.

Couch B A, DeMarco G J, Gourley S L, Koleske A J, Increased Dendrite Branching in AβPP/PS1 Mice and Elongation of Dendrite Arbors by Fasudil Administration. Alzheimers Dis. 2010; 20(4): 1003-1008.

Erkinjuntti T, Inzitari D, Pantoni L, Wallin A, Scheltens P, Rockwood K, Desmond D W. 2000. Limitations of clinical criteria for the diagnosis of vascular dementia in clinical trials. Is a focus on subcortical vascular dementia a solution? Ann N Y Acad Sci. 903:262-72.

Feng Y, LoGrasso P, Defert O, Li R, Rho Kinase (ROCK) Inhibitors and Their Therapeutic Potential. J Med Chem. 2016; 59*6): 2269-2300.

Folstein M F, Folstein S E, McHugh P R. "Mini-mental state": a practical method for grading the cognitive state of patients for the clinician. J Psychiatr Res. 1975; 12:189-198.

Hamano T, Shirafuji N; Yen S; Yoshida H, Kanaan N, Hayashi K, Ikawa M, Yamamura O, Fujita Y; Kuriyama M, Nakamoto Y, Rho-kinase ROCK inhibitors reduce oligomeric tau protein. Neurobiology of Aging; 2020; 89: 41-54.

Hou Y, Zhou L, Yang Q D, Du X P, Li M, Yuan M, Zhou Z W, Changes in hippocampal synapses and learning-memory abilities in a streptozotocin-treated rat model and intervention by using fasudil hydrochloride. Neuroscience. 2012; 200: 120-129.

Human Rights Watch. 2018. They Want Docile: How Nursing Homes in the United States Overmedicate People with Dementia. ISBN: 978-1-623-135720. Downloaded 17 May 2019 from http://www.hrw.org.

Jacobs M, Hayakawa K, Swenson L, Bellon S, Fleming M, Taslimi P, Doran J, The structure of dimeric ROCK I reveals the mechanism for ligand selectivity. J Biol Chem. 2006; 281(1): 260-68.

Kamei S, Oishi M, Takasu T. 1996a. Evaluation of fasudil hydrochloride treatment for wandering symptoms in cerebrovascular dementia with 31P-magnetic resonance spectroscopy and Xe-computed tomography. Clin Neuropharmacol. 19:428-38.

Kamei S, Toshiaki T, Oishi M, Effect of fasudil hydrochloride on wandering symptoms of c cerebrovascular dementia patients. Neurotherapy. 1996b 13:43-50.

Kim K W, Lee D Y, Jhoo J H, Youn J C, Suh Y J, Jun Y H, Seo E H, Woo J I, Diagnost accuracy of mini-mental status examination and revised Hasegawa dementia scale for Alzheimer's disease. Dement Geriatr Cogn Disord. 2005; 19(5-6):324-30.

Klein D A, Steinberg M, Galik E, Steele C, Sheppard J M, Warren A, Rosenblatt A, Lyketsos C, Wandering behaviour in community-residing persons with dementia. Intl J Geriatric Psychiatry. 1999.14(4): 272-279.

Knuffman J, Mohsin F, Feder J, Grossberg G T. 2001. Differentiating between lewy body dementia and Alzheimer's disease: a retrospective brain bank study. J Am Med Dir Assoc. 2:146-48.

Lai C K, Arthur D G. Wandering behaviour in people with dementia. J Adv Nurs. 2003; 44(2):173-182.

Logsdon R, Teri L, Mccurry S, Gibbons L E, Kukull W A, Larson E B, Wandering: A Significant Problem among Community Residing Individuals with Alzheimer's Disease. The Journals of Gerontology Series B Psychological Sciences and Social Sciences. 1998; 53(5):P294-9.

Nakagawa O, Fukisawa K, Ishizaki T, Saito Y, Nakao K, Narumiya S, ROCK-I and ROCK-II, two isoforms of Rho-associated coiled-coil forming protein serine/threonine kinase in mice. FEBS Lett. 1996 Aug. 26; 392(2): 189-93.

Nakaoka A, Suto S, Makimoto K, Yamakawa M, Shigenobu K, Tabushi K. 2010. Pacing and lapping movements among institutionalized patients with dementia. Am J Alzheimers Dis Other Demen. 25:167-72.

Nelson & Algase (Eds) Evidence-based Protocols for Wandering Behaviour (2006), Springer:NY. Risk Model.

Román GC, Tatemichi T K, Erkinjuntti T, Cummings J L, Masdeu J C, Garcia J H, Amaducci L, Orgogozo J M, Brun A, Hofman A, et al. 1993. Vascular dementia: diagnostic criteria for research studies. Report of the NINDS-AIREN International Workshop. Neurology. 43:250-60.

Román GC. 2004. Facts, myths, and controversies in vascular dementia. J Neurol Sci. 226:49-52.

Rovner B W, Folstein M F. Mini-mental state exam in clinical practice. Hosp Pract. 1987; 22(1A):99, 103, 106, 110.

Salardini A. 2019. An Overview of Primary Dementias as Clinicopathological Entities. Semin Neurol. 39:153-166.

Sasaguri H, Nilsson P, Hashimoto S, Nagata K, Saito T, De Strooper B, Hardy J, Vassar R, Winblad B, Saido T C, APP mouse models for Alzheimer's disease preclinical studies. EMBO J. 2017; 36(17): 2473-2487.

Sellers K, Elliott C, Jackson J, Ghosh A, Ribe E, Rojo A, Jarosz-Griffiths H H, Watson A A, Xia W, Semenov M, Morin P, Hooper N, Porter R, Preston J, Al-Shawi R, Baillie G, Lovestone S Cuadrado A, Harate M, Simons P, Srivastava D P, Killick R, Amyloid B synaptotoxicity is Wnt-PCP dependent and blocked by fasudil. Alzeimer's & Dementia. 2018; 14: 306-317.

Shibuya M, Asano T, Sasaki Y. 2001. Effect of Fasudil HCl, a protein kinase inhibitor, on cerebral vasospasm. Acta Neurochir Suppl. 77:201-4.

Turk M. The Effect of Rho Kinase Inhibitors on Alzheimer's Disease, Dissertation. Arizona State University. May 2017.

Uehata M, Ishizaki T, Satoh H, Ono T, Kawahara T, Morishita T, Tamakawa H, Yamagami K, inui J, Maekawa M, Narumiya S, Calcium sensitization of smooth muscle mediated by a Rho-associated protein kinase in hypertension. Nature. 1997 Oct. 30; 389(6654):990-4.

US Census: www.census.gov

Wetterling T, Kanitz R D, Borgis K J. 1996. Comparison of different diagnostic criteria for vascular dementia (ADDTC, DSM-IV, ICD-10, NINDS-AIREN). Stroke. 27:30-6.

Wick J Y, Zanni G R. Aimless excursions: wandering in the elderly. Consult Pharm. 2006; 21(8):608-612, 615-618.

Yamaguchi H, Miwa Y, Kasa M, Kitano K, Amano M, Kaibuchi K, Hakoshima T, Structural basis for induced-fit binding of Rho-kinase to the inhibitor Y-27632. J Biochem. 2006 September; 140(3):305-11.

Yayama S, Yamakawa M, Suto S, Greiner C, Shigenobu K, Makimoto K. 2013. Discrepancy between subjective and objective assessments of wandering behaviours in dementia as measured by the Algase Wandering Scale and the Integrated Circuit tag monitoring system. Psychogeriatrics. 13:80-7.

Yu J, Gu Q, Yan Y, Yu H, Guo M, Liu C, Song G, Chai Z, Wang Q, Zia B, Zhang H, Jiang Y, Cungen M A, Fausidil improves cognition of APP/PS1 transgenic mice via inhibiting the activation of microglia and shifting microglia phenotypes from M1 to M2. Chin J Cell Mol Immunol. 2017; 33(12): 1585-1593.

The disclosure of each reference set forth herein is incorporated herein by reference in its entirety.

The invention claimed is:

1. A method of treating wandering in a patient with Alzheimer's disease, comprising treating the patient with at least 60 mg/day of fasudil, wherein the fasudil is orally administered.

2. The method of claim 1, where the patient has not previously been treated with fasudil for chronic stroke.

3. The method of claim 1, wherein the patient does not display a wayfinding defect.

4. The method of claim 1, wherein the patient engages in elopement, escape or boundary transgressions.

5. The method according to claim 1, wherein the patient is a sporadic wanderer.

6. The method of claim 1, wherein the patient is a persistent wanderer who is in motion at least 20% of waking hours, comprising treating said patient with a therapeutically effective amount of fasudil.

7. The method of claim 1, wherein the patient does not have pseudobulbar affect.

8. The method according to claim 1, wherein the fasudil is orally administered as fasudil hydrochloride hemihydrate at a dose of 70 to 120 mg/day.

9. The method according to claim 8, wherein the fasudil is orally administered at a dose of 90 mg/day.

10. The method according to claim 9, wherein the fasudil is orally administered two or three times per day.

11. The method according to claim 1, wherein the fasudil reduces the number of days per week the patient wanders.

12. The method according to claim 9, wherein the fasudil reduces the number of days per week the patient wanders.

13. The method according to claim 1, wherein the fasudil is fasudil hydrochloride hemihydrate.

14. The method according to claim 1, wherein the patient is treated for at least 6 months.

15. The method according to claim 1, wherein the fasudil reduces the number of days per week the patient wanders.

* * * * *